(12) United States Patent
Kim

(10) Patent No.: US 11,703,508 B2
(45) Date of Patent: Jul. 18, 2023

(54) LIPIDOMICS-BASED IDENTIFICATION OF PATIENTS BEARING OVARIAN TUMORS

(71) Applicant: The Feinstein Institutes for Medical Research, Manhasset, NY (US)

(72) Inventor: Junhwan Kim, New Hyde Park, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 503 days.

(21) Appl. No.: 16/841,968

(22) Filed: Apr. 7, 2020

(65) Prior Publication Data

US 2020/0319190 A1    Oct. 8, 2020

Related U.S. Application Data

(60) Provisional application No. 62/830,699, filed on Apr. 8, 2019.

(51) Int. Cl.
  *G01N 33/574* (2006.01)
  *G01N 33/92* (2006.01)
  *A61K 35/16* (2015.01)
  *A61K 47/60* (2017.01)

(52) U.S. Cl.
  CPC ....... *G01N 33/57449* (2013.01); *A61K 35/16* (2013.01); *A61K 47/60* (2017.08); *G01N 33/92* (2013.01); *G01N 2405/04* (2013.01)

(58) Field of Classification Search
  CPC ............ G01N 33/57449; G01N 33/92; G01N 2405/04; A61K 35/16
  See application file for complete search history.

(56) References Cited

PUBLICATIONS

National Comprehensive Cancer Network, Clinical practice guidelines in Ovarian Cancer, Version 4.2017, Nov. 9, 2017. (Year: 2017).*
Kim et al., "Comprehensive Approach to the Quantitative Analysis of Mitochondrial Phospholipids by HPLC-MS," J. Chromatogr. B. Analyt. Technol. Biomed Life Sci., vol. 912, Jan. 1, 2013, pp. 105-114.
Xu et al., "Lysophosphatidic Acid as a Potential Biomarker for Ovarian and Other Gynecologic Cancers," JAMA, vol. 280, No. 8, Aug. 26, 1998, pp. 719-723.
Yagi et al., "Challenges and Inconsistencies in Using Lysophosphatidic Acid as a Biomarker for Ovarian Cancer," Cancers, vol. 11, No. 520, Apr. 11, 2019, pp. 1-13.
Yagi et al., "Relative Ratios Enhance the Diagnostic Power of Phospholipids in Distinguishing Benign and Cancerous Ovarian Masses," Cancers, vol. 12, No. 72, Dec. 26, 2019, pp. 1-14.

* cited by examiner

*Primary Examiner* — Elly-Gerald Stoica
(74) *Attorney, Agent, or Firm* — Amster, Rothstein & Ebenstein LLP

(57) ABSTRACT

Methods are disclosed for treating ovarian tumors and ovarian and pancreatic cancers using computed and normalized relative ratios of plasma levels of phospholipids, particularly lysophosphatidylcholine, lysophosphatidylethanolamine, phosphatidylcholine, phosphatidylethanolamine and sphingomyelin.

5 Claims, 7 Drawing Sheets

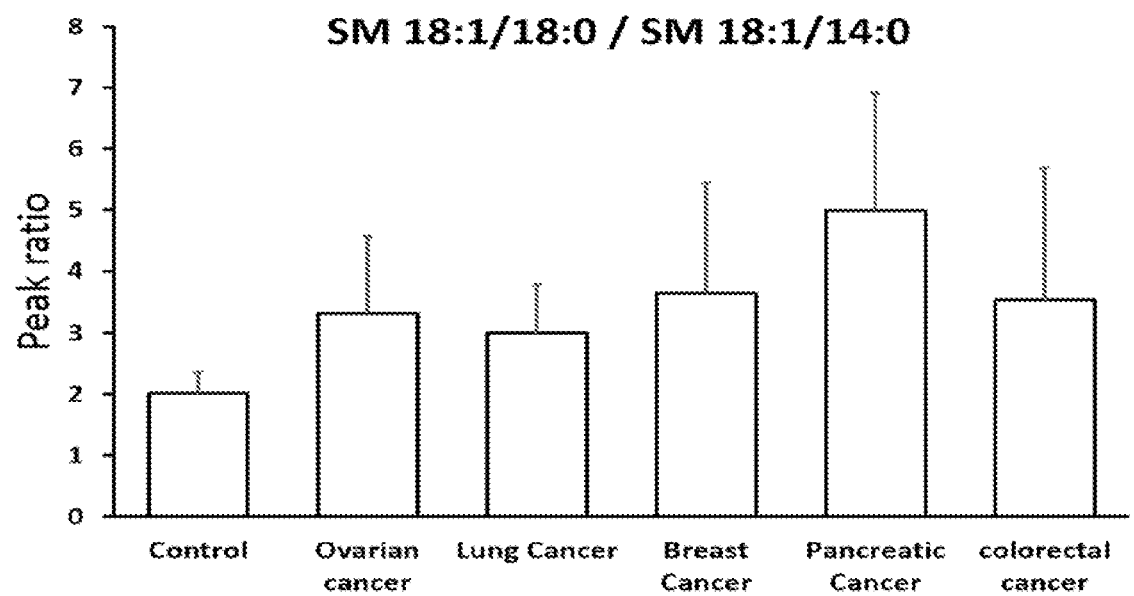
FIG. 6
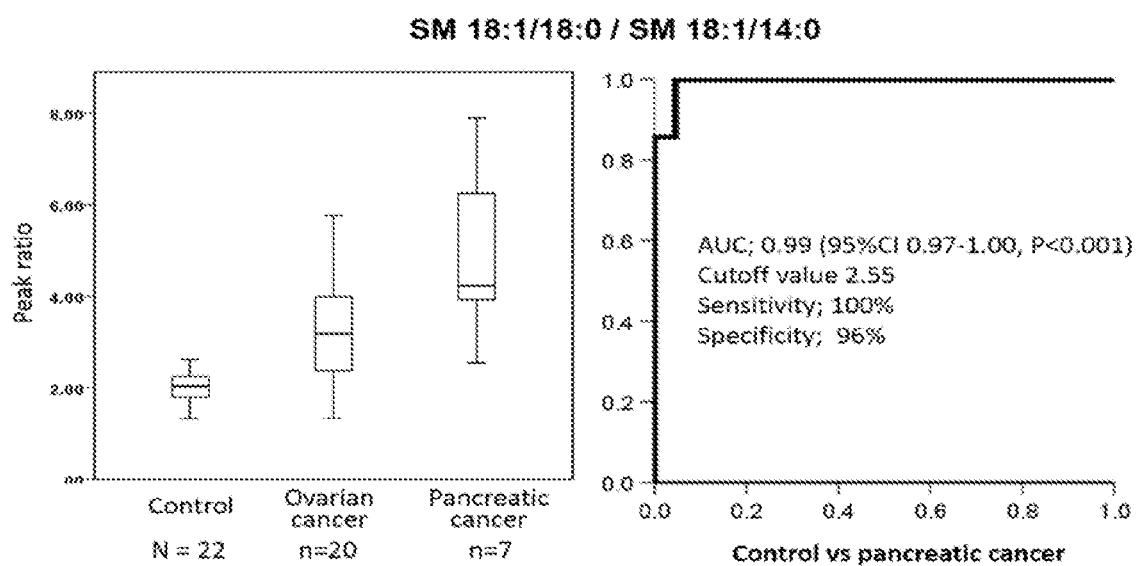
FIG. 7A                    FIG. 7B

LIPIDOMICS-BASED IDENTIFICATION OF PATIENTS BEARING OVARIAN TUMORS

CROSS-REFERENCE TO RELATED APPLICATION

This application claims the benefit of U.S. Provisional Patent Application No. 62/830,699, filed on Apr. 8, 2019, the contents of which are herein incorporated by reference into the subject application.

BACKGROUND OF THE INVENTION

Throughout this application various publications are referred to in brackets. Full citations for these references may be found at the end of the specification immediately preceding the claims. The disclosures of these publications are hereby incorporated by reference in their entireties into the subject application to more fully describe the art to which the subject application pertains.

Ovarian cancer has the highest mortality among gynecological cancers despite remarkable advances in the knowledge of molecular biology and treatment [De Angelis, 2014; Santaballa, 2016]. The American Cancer Society estimates that in 2018, about 22,240 new cases of ovarian cancer will be diagnosed and 14,070 women will die of ovarian cancer in the United States. This high mortality is attributable to the lack of subjective symptoms or reliable biomarkers, which aid in establishing early diagnosis. For example, the sensitivity of the cancer antigen 125 (CA-125) tumor marker for the detection of non-advanced epithelial ovarian cancer is detected only in approximately 50% of patients with stage I ovarian cancer. Thus, this marker alone is not recommended to distinguish between a benign and a malignant adnexal mass [Biggs, 2016; Schwartz, 1995]. Furthermore, pelvic examination and imaging tests are commonly used to confirm the presence of a pelvic mass but are unable to distinguish between a benign and a malignant tumor. The final diagnosis of benign or malignant adnexal mass is determined by the pathological examination of a surgically removed tumor [Santaballa, 2016].

As such, an extensive effort has been made to find circulating markers with better sensitivity and specificity. The most promising outcome has been reported from proteomics-based approaches [Montagnana, 2017]. Since the successful screening study shown by Petricoin et al. [2002], various protein markers have been identified [Ye, 2003; Jackson, 2007]. However, the clinical application of proteomics is limited due to many challenges, especially the necessity of sample preconditioning steps to reduce interference from more abundant proteins [Ye, 2006; Jackson, 2007]. Presently, only CA-125 and human epididymis protein 4 have been approved as biomarkers for clinical application. The combination of these two makers in an algorithm helps to determine the risk of malignancy and has been approved by Food and Drug Administration (FDA).

Phospholipids, including lysophospholipids (FIG. 1) and sphingomyelin, have been an unrecognized potential source of ovarian cancer biomarkers, although they are highly abundant in plasma. On one hand, studies focusing on lysophospholipids reported multiple lysophosphatidic acid (LPA) species as potential diagnostic markers; however, there remains significant discrepancy regarding the utility of lysophosphatidic acid. On the other hand, a global lipidomics approach has revealed differences in plasma lipid profiles between ovarian cancer patients and healthy controls but has failed to identify specific markers with acceptable sensitivity and specificity [Zhang, 2016].

Because of the lack of symptoms, more than 75% of ovarian cancer patients are diagnosed at advanced stages such as stage III or IV. The 5-year survival rate at stages III-IV is about 30%, whereas the survival rate is over 90% at stages I-II. Therefore, having a sensitive and specific early diagnostic biomarker has the potential to improve screening for ovarian cancer and significantly improve survival rate through early identification of malignancy and guiding best practices choice of appropriate therapeutic approach, including the possible enrollment in clinical trials. Currently, there is no biomarker that can be used reliably in the treatment of ovarian cancer at early stages of the disease. The present application addresses the need for treatment of ovarian and other cancers, in accordance with the identification of patients at early stages of disease by the calculation of certain indicative ratios of circulating lipids.

SUMMARY OF THE INVENTION

The present invention is directed to methods for diagnosing and treating ovarian tumors and ovarian and pancreatic cancer using plasma levels of one or more of phospholipids such as phosphatidylcholine (PC), phosphatidylethanolamine (PE) including phosphatidylethanolamine plasmalogen (PEP), sphingomyelin (SM), lysophosphatidylethanolamine (LPE) including lysophosphatidylethanolamine plasmalogen (LPEP) and/or lysophosphatidylcholine (LPC), and ratios thereof, as biomarkers for identification and treatment of ovarian and pancreatic cancers.

BRIEF DESCRIPTION OF THE DRAWINGS

FIG. 6. Ratio of SM 18:1/18:0/SM 18:1/14:0 in pancreatic cancer compared to other cancers and control (P<0.001 vs Control, P=0.027 vs Ovarian cancer, P=0.021 vs Lung cancer, P=0.083 vs Breast cancer, P=0.064 vs colorectal cancer; n=22 for Control, 20 for ovarian cancer, 8 for lung cancer, breast cancer and colorectal cancer, and 7 for pancreatic cancer).

FIG. 7A-7B. Receiver operating characteristic analysis of phospholipids ratio SM 18:1/18:0/SM 18:1/14:0. A) Peak ratios in Control, Ovarian Cancer and Pancreatic Cancer. B) The area under the curve (AUC) of the capacity of the ratio of SM 18:1/18:0/SM 18:1/14:0 to differentiate pancreatic cancer from control was 0.99.

DETAILED DESCRIPTION OF THE INVENTION

Figure 1:
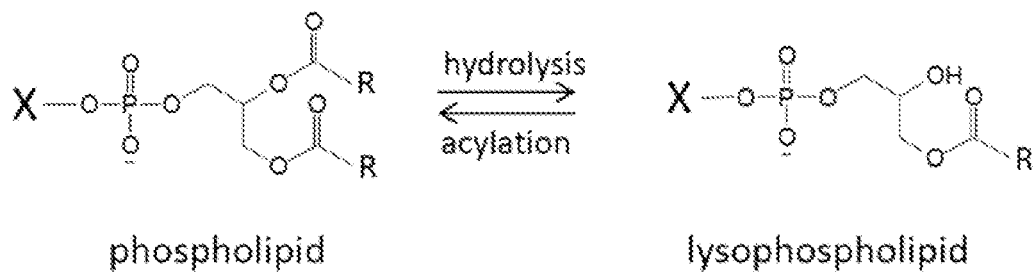
FIG. 1. The structure of phospholipids and lysophospholipids. X represents head groups that determine the class of phospholipids and R represents alkyl chains that determine species within a class of phospholipids. Abundant classes of phospholipids found in plasma are phosphatidylcholine, phosphatidylethanolamine, and phosphatidylinositol, and corresponding lysophospholipids. The common acyl chains include palmitic acids (16:0), stearic acid (18:0), oleic acid (18:1) linoleic acid (18:2), arachidonic acid (20:4), and docosahexaenoic acid (22:6).

The invention provides a method of treating a cancer in a patient, the method comprising
I) a) receiving an identification of the patient as having ovarian cancer; and
b) administering to the patient identified as having ovarian cancer one or more of a therapeutic program of watchful waiting, laparoscopy, biopsy, chemotherapy, radiation therapy, immunotherapy, hormonal therapy or surgery effective to treat ovarian cancer in a patient,
wherein the patient is identified as having ovarian cancer if an assay of phospholipids having been obtained from a plasma sample from the patient determined one or both of i) or ii):
i) one or more of the ratio of lysophosphatidylcholine (LPC), LPC20:4/LPC18:0, LPC22:6/LPC18:0, LPC20:4/LPC16:0, LPC22:6/LPCP16:0, and/or sphingomyelin (SM), SM18:1/24:1/SM18:1/22:0, obtained from the plasma of the patient is elevated compared to the level from a control group of women without an ovarian tumor or ovarian cancer; or
ii) one or more of the ratio of sphingomyelin (SM), SM18:1/24:1/SM18:1/22:0, SM18:1/16:0/SM18:1/22:0, SM18:1/16:0/SM 18:1/14:0, SM18:1/24:1/SM18:1/14:0, and/or phosphatidylethanolamine (PE), PE16:0/18:1/PEP18:0/18:2 obtained from the plasma of the patient is elevated compared to the level from a group of women with a benign ovarian tumor; or
II) a) receiving an identification of the patient as having pancreatic cancer; and
b) administering to the patient identified as having pancreatic cancer one or more of a therapeutic program of watchful waiting, laparoscopy, biopsy, chemotherapy, radiation therapy, immunotherapy, hormonal therapy or surgery effective to treat pancreatic cancer in a patient,
wherein the patient is identified as having pancreatic cancer if an assay of phospholipids having been obtained from a plasma sample from the patient determined the ratio of sphingomyelin (SM), SM18:1/18:0/SM18:1/14:0 obtained from the plasma of the patient is elevated compared to the level from a control group of subjects without pancreatic cancer.

The invention also provides a method for treating a patient with a cancer, the method comprising the steps of:

I) a) identifying whether the patient has ovarian cancer by
obtaining or having obtained a plasma sample from the patient, and
performing or having performed an assay on the plasma sample to identify whether the patient has ovarian cancer,
wherein the patient is identified as having ovarian cancer if an assay of phospholipids having been obtained from a plasma sample from the patient determined one or both of i) or ii):
i) one or more of the ratio of lysophosphatidylcholine (LPC), LPC20:4/LPC18:0, LPC22:6/LPC18:0, LPC20:4/LPC16:0, LPC22:6/LPCP16:0, and/or sphingomyelin (SM) 18:1/24:1/SM18:1/22:0 obtained from the plasma of the patient is elevated compared to the level from a control group of women without an ovarian tumor or ovarian cancer; or
ii) one or more of the ratio of sphingomyelin (SM), SM18:1/24:1/SM18:1/22:0, SM18:1/16:0/SM18:1/22:0, SM18:1/16:0/SM 18:1/14:0, SM18:1/24:1/SM18:1/14:0, and/or phosphatidylethanolamine (PE), PE16:0/18:1/PEP18:0/18:2 obtained from the plasma of the patient is elevated compared to the level from a group of women with a benign ovarian tumor; and
b) administering to the patient identified as having ovarian cancer one or more of a therapeutic program of watchful waiting, laparoscopy, biopsy, chemotherapy, radiation therapy, immunotherapy, hormonal therapy or surgery effective to treat ovarian cancer in a patient; or
II) a) identifying whether the patient has pancreatic cancer by
obtaining or having obtained a plasma sample from the patient, and
performing or having performed an assay on the plasma sample to identify whether the patient has pancreatic cancer,
wherein the patient is identified as having pancreatic cancer if an assay of phospholipids having been obtained from a plasma sample from the patient determined the ratio of sphingomyelin (SM), SM18:1/18:0/SM18:1/14:0, obtained from the plasma of the patient is elevated compared to the level from a control group of subjects without pancreatic cancer; and
b) administering to the patient identified as having pancreatic cancer one or more of a therapeutic program of watchful waiting, laparoscopy, biopsy, chemotherapy, radiation therapy, immunotherapy, hormonal therapy or surgery effective to treat pancreatic cancer in a patient.

In one embodiment, the patient has ovarian cancer. In one embodiment, the patient is identified as having ovarian cancer if an assay of phospholipids having been obtained from a plasma sample from the patient determined one or more of the ratio of lysophosphatidylcholine (LPC), LPC20:4/LPC18:0, LPC22:6/LPC18:0, LPC20:4/LPC16:0, LPC22:6/LPCP16:0, and/or sphingomyelin (SM), SM18:1/24:1/SM18:1/22:0, obtained from the plasma of the patient is elevated compared to the level from a control group of women without an ovarian tumor or ovarian cancer. In one embodiment, the patient is identified as having ovarian cancer if an assay of phospholipids having been obtained from a plasma sample from the patient determined one or more of the ratio of sphingomyelin (SM), SM18:1/24:1/SM18:1/22:0, SM18:1/16:0/SM18:1/22:0, SM18:1/16:0/SM 18:1/14:0, SM18:1/24:1/SM18:1/14:0, and/or phosphatidylethanolamine (PE), PE16:0/18:1/PEP18:0/18:2 obtained from the plasma of the patient is elevated compared to the level from a group of women with a benign ovarian tumor. In one embodiment, the patient has pancreatic cancer.

The invention further provides a method of treating a benign ovarian tumor in a patient, the method comprising
 a) receiving an identification of the patient as having a benign ovarian tumor; and
 b) administering to the patient identified as having a benign ovarian tumor one or more of a therapeutic program of watchful waiting, laparoscopy, biopsy, chemotherapy, radiation therapy, immunotherapy, hormonal therapy or surgery effective to treat a benign ovarian tumor in a patient,
 wherein the patient is identified as having a benign ovarian tumor if an assay of phospholipids having been obtained from a plasma sample from the patient determined one or more of the ratio of phosphatidylcholine (PC)18:0/20:4/PC18:0/18:1, lysophosphatidylethanolamine (LPE), LPE22:6/LPEP16:0, lysophosphatidylcholine (LPC), LPC22:6/LPC18:0, LPC20:4/LPC18:0 and/or phosphatidylcholine (PC), PC18:0/22:6/PC18:0/18:1, obtained from the plasma of the patient is elevated compared to the level from a control group of women without an ovarian tumor or ovarian cancer.

The invention also provides a method for treating a patient with a benign ovarian tumor, the method comprising the steps of:
 a) identifying whether the patient has a benign ovarian tumor by
  obtaining or having obtained a plasma sample from the patient, and
  performing or having performed an assay on the plasma sample to identify whether the patient has a benign ovarian tumor,
  wherein the patient is identified as having a benign ovarian tumor if an assay of phospholipids having been obtained from a plasma sample from the patient determined one or more of the ratio of phosphatidylcholine (PC), PC18:0/20:4/PC18:0/18:1, lysophosphatidylethanolamine (LPE), LPE22:6/LPEP16:0, lysophosphatidylcholine (LPC), LPC22:6/LPC18:0, LPC20:4/LPC18:0 and/or phosphatidylcholine (PC), PC18:0/22:6/PC18:0/18:1, obtained from the plasma of the patient is elevated compared to the level from a control group of women without an ovarian tumor or ovarian cancer; and
 b) administering to the patient identified as having a benign ovarian tumor one or more of a therapeutic program of watchful waiting, laparoscopy, biopsy, chemotherapy, radiation therapy, immunotherapy, hormonal therapy or surgery effective to treat a benign ovarian tumor in a patient.

The invention further provides a method for diagnosing an ovarian cancer in a patient, the method comprising the steps of:
 obtaining or having obtained a plasma sample from the patient, and
 performing or having performed an assay on the plasma sample to identify whether the patient has ovarian cancer,
 wherein the patient is identified as having ovarian cancer if an assay of phospholipids having been obtained from a plasma sample from the patient determined one or both of i) or ii):
  i) one or more of the ratio of lysophosphatidylcholine (LPC), LPC20:4/LPC18:0, LPC22:6/LPC18:0, LPC20:4/LPC16:0, LPC22:6/LPCP16:0, and/or sphingomyelin (SM), SM18:1/24:1/SM18:1/22:0, obtained from the plasma of the patient is elevated compared to the level from a control group of women without an ovarian tumor or ovarian cancer; or
  ii) one or more of the ratio of sphingomyelin (SM), SM18:1/24:1/SM18:1/22:0, SM18:1/16:0/SM18:1/22:0, SM18:1/16:0/SM 18:1/14:0, SM18:1/24:1/SM18:1/14:0, and/or phosphatidylethanolamine (PE). PE16:0/18:1/PEP18:0/18:2 obtained from the plasma of the patient is elevated compared to the level from a group of women with a benign ovarian tumor.

The invention also provides a method for diagnosing a benign ovarian tumor in a patient, the method comprising the steps of:
 obtaining or having obtained a plasma sample from the patient, and
 performing or having performed an assay on the plasma sample to identify whether the patient has a benign ovarian tumor,
 wherein the patient is identified as having a benign ovarian tumor if an assay of phospholipids having been obtained from a plasma sample from the patient determined one or more of the ratio of phosphatidylcholine (PC), PC18:0/20:4/PC18:0/18:1, lysophosphatidylethanolamine (LPE), LPE22:6/LPEP16:0, lysophosphatidylcholine (LPC), LPC22:6/LPC18:0, LPC20:4/LPC18:0 and/or PC18:0/22:6/PC18:0/18:1 obtained from the plasma of the patient is elevated compared to the level from a control group of women without an ovarian tumor or ovarian cancer.

Preferably, the assay is or has been performed using HPLC-mass spectrometry.

In the methods described herein, phospholipids can be normalized by a process comprising one or more of normalizing peak areas to internal standards, where phospholipid species are normalized to 1,2-dipalmitoyl-sn-glycero-3-phospho-N-methylethanolamine (PME), and lysophosphatidylethanolamine (LPE) and lysophosphatidylcholine (LPC) species are normalized to LPE (17:1) and LPC (17:1), respectively; individual phospholipid species are normalized to the total content of the class of phospholipids; and peak ratios are obtained by comparing phospholipids.

Preferably, the patient is a human.

Treatment options for ovarian tumors and ovarian and pancreatic cancer include one or more of a therapeutic program of watchful waiting, laparoscopy, biopsy, surgical removal of the tumor, chemotherapy, radiation therapy, immunotherapy and hormonal therapy.

Also provided are the use of plasma levels of one or more of phospholipids phosphatidylcholine (PC), phosphatidylethanolamine (PE) including phosphatidylethanolamine plasmalogen (PEP), sphingomyelin (SM), lysophosphatidylethanolamine (LPE) including lysophosphatidylethanolamine plasmalogen (LPEP) and/or lysophosphatidylcholine (LPC), and ratios thereof, for diagnosis and treatment of an ovarian tumor or ovarian cancer or pancreatic cancer in a patient.

The individual phospholipids mentioned herein have been previously described; see, for example, PubChem, the open chemistry database (pubchem.ncbi.nlm.nih.gov).

"And/or" as used herein, for example, with option A and/or option B, encompasses the embodiments of (i) option A, (ii) option B, and (iii) option A plus option B.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Materials and Methods

Introduction.

The current study focused on investigation of circulating phospholipids, including sphingophospholipids in ovarian cancer. Using an established liquid chromatography-mass spectrometry (LC-MS) method, phospholipid levels were compared in plasma samples obtained from patients with stage III ovarian cancer, patients with benign ovarian tumors, and non-cancer controls. Multiple phospholipid species were found that have various concentrations among control, benign, and cancer groups.

Materials and Reagents.

Reagent-grade chemicals and HPLC-grade solvents were purchased from major commercial suppliers (Fisher Scientific and Sigma Aldrich). Internal standards, 1,2-dipalmitoyl-sn-glycero-3-phospho-N-methylethanolamine (PME) was purchased from Santa Cruz Biotech (Santa Cruz, Calif.), and 1-(10Z-heptadecenoyl)-2-hydroxy-sn-glycero-3-phosphocholine (LPC (17:1)) and 1-(10Z-heptadecenoyl)-sn-glycero-3-phosphoethanolamine (LPE (17:1)) were purchased from Avanti Polar Lipids (Alabaster, Ala., USA). Milli-Q water was used throughout.

Samples.

All plasma samples were collected under protocols approved by the Institutional Review Board at the Feinstein Institute for Medical Research. Informed consent was not obtained as no individually identifiable data were collected. Frozen plasma samples collected from three groups, patients with confirmed stage I to IV ovarian cancer (cancer), benign ovarian tumors (benign), and health, non-cancer pathology (control), were used. Table 1 shows patients and tumors characteristics. Plasma fractions were separated from blood specimens collected in EDTA containing tubes using centrifugation and stored at −80° C. until analyzed.

Extraction of Phospholipids.

Lipids were extracted from the plasma samples following published methods [Zhao, 2010]. Briefly, 50 µL of previously frozen plasma was extracted with 750 µL of methanol in the presence of 0.1 nmol of PME, 0.15 nmol of LPE (17:1), and 0.85 nmol of LPC (17:1) as internal standards. The mixture was vortexed for 2 minutes, incubated for 10 minutes at 4° C., and centrifuged for 10 minutes at 16,000 g. The supernatant was decanted and evaporated to dryness under $N_2$. The residue was reconstituted in a 100 µL of solution containing isopropanol (IPA):t-butyl methyl ether (TBME):aqueous ammonium formate (94 mM) (34:17:5, v:v:v). Finally, 20 µL of the solution was injected into the HPLC-MS.

HPLC Ms Analysis.

The phospholipid mixture was analyzed using normal-phase HPLC-MS [Kim, 2013; Choi, 2018]. Eluent A was created using IPA:TBME:aqueous ammonium formate (94 mM, pH ~2.5) (34:17:5, v:v:v) with eluent B containing 100% MeOH. The gradients used for the 35 minutes chromatogram were as follows: 100% A for 18 minutes, 100% A to 20% A over 6 minutes, 20% A for 3 minutes, 20% A to 100% A over 1 minutes, and hold 100% A for 7 minutes. The flow rate was 0.3 mL/min and the column temperature was 30° C. MS and MS/MS data were obtained with an LTQ XL spectrometer (Thermo Scientific, San Jose, Calif.) operated in the negative ion mode.

Data Analysis.

Obtained data were processed using Thermo X-calibur software (version 2.2) {Kim, 2015 #136}. Retention time and MS and MS/MS data were compared to the control to identify individual species (FIG. 2, step a) [Kim, 2015]. The concentration of phosphatidylethanolamine (PE) and phosphatidylcholine (PC) includes plasmalogens, which contain an ether linkage at the sn-1 position [Choi, 2018]. PE and PC plasmalogens were denoted as PEP and PCP, respectively. Species between diacyl PE and PEP were distinguished based on their molecular weights and fragmentation patterns by MS/MS. The peak areas of individual species were calculated using M0 and M1 peaks.

Peak Normalization.

Figure 2:
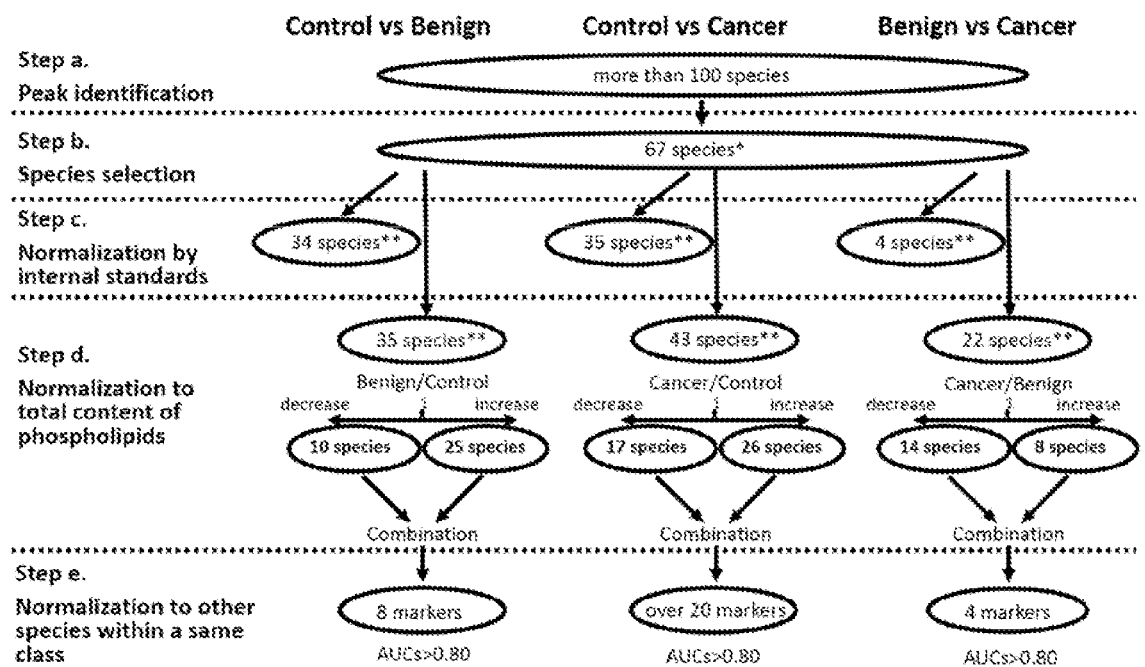
FIG. 2. Flow chart for biomarker selection procedure. Unstable phospholipid species and minor species were excluded from analysis. * denotes quantifiable and stable species, and ** denotes significant different between two groups ($p<0.05$).
Figure 3A:
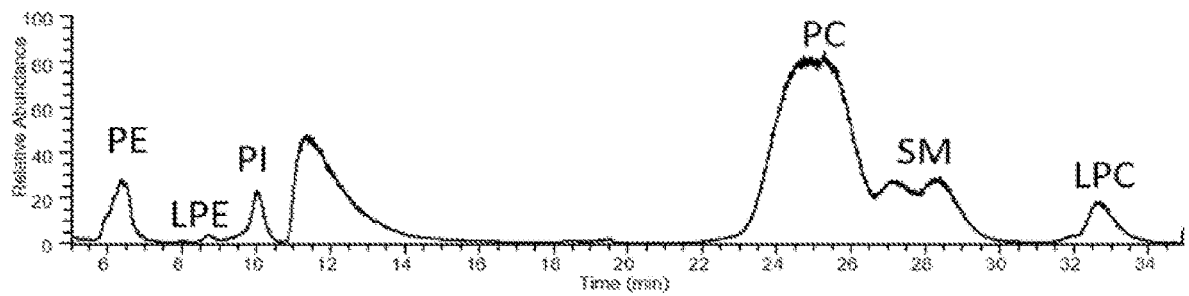
FIG. 3A-3G. Total ion chromatogram and MS spectra of plasma phospholipids. HPLC-MS analysis (A) and MS spectra of phosphatidylethanolamine (PE) (B), phosphatidylinositol (PI) (C), phosphatidylcholine (PC) (D), sphingomyelin (SM) (E), lysophosphatidylethanolamine (LPE) (F), and lysophosphatidylcholine (LPC) (G).
Figure 3B:
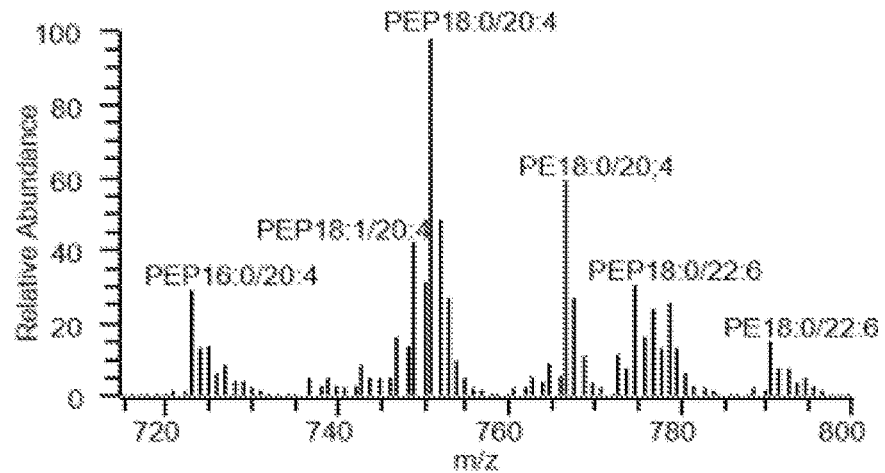
Figure 3C:
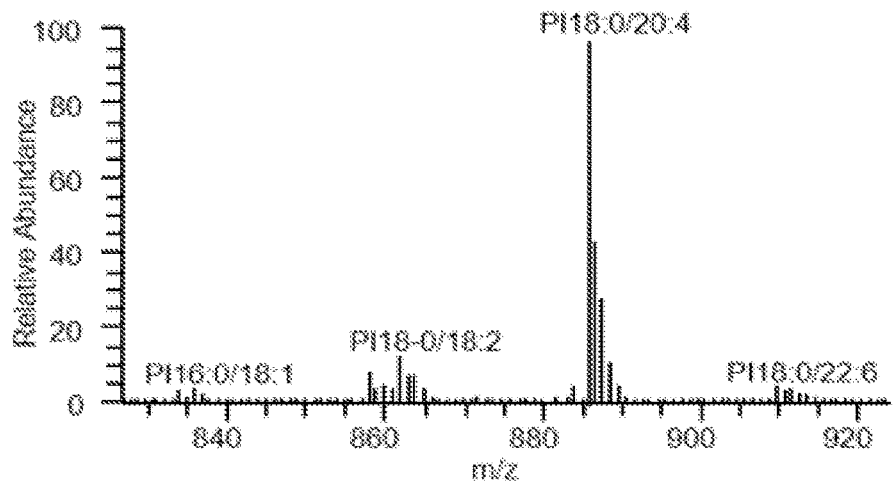
Figure 3D:
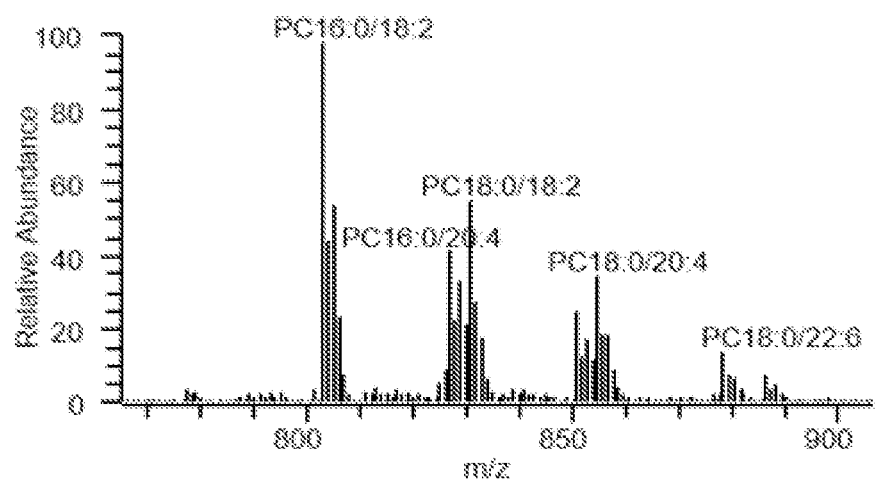
Figure 3E:
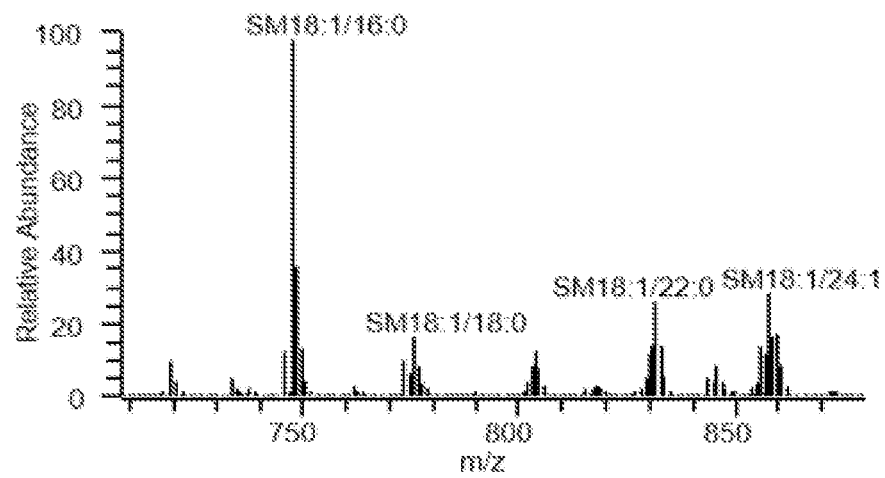
Figure 3F:
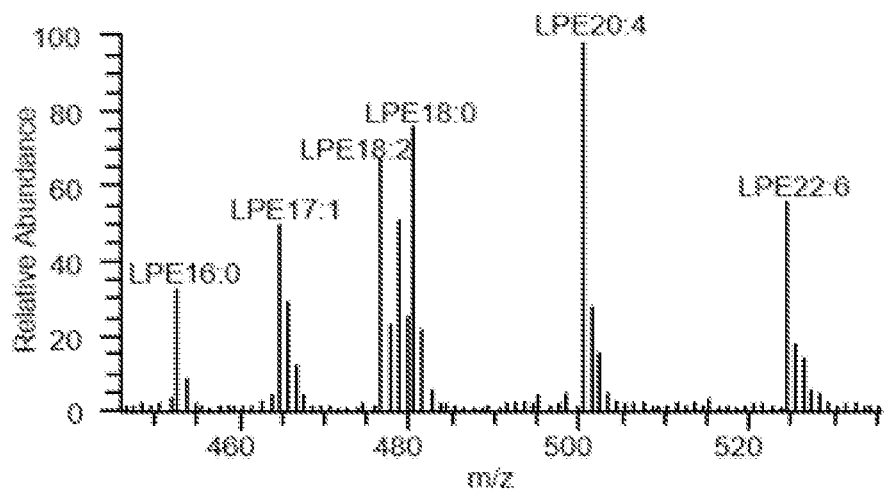
Figure 3G:
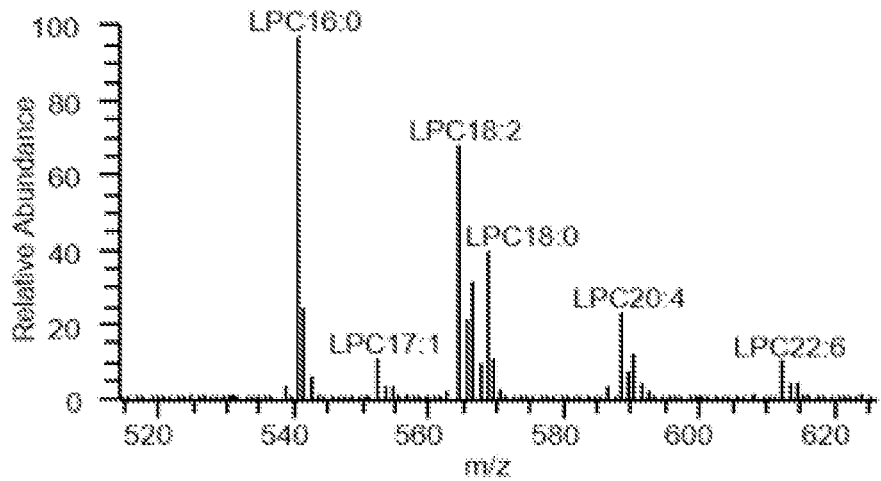

Three different approaches were used for peak normalization. 1) Peak areas were normalized to the internal standards (FIG. 2, step c), (i.e., phospholipids species were normalized to PME [Kim, 2013], while lysophosphatidylethanolamine (LPE) and lysophosphatidylcholine (LPC) species were normalized to LPE (17:1) and LPC (17:1), respectively). This standard quantitation approach yielded subtle differences in phospholipid profiles between the three groups. 2) Individual phospholipid species were normalized to the total content of the class of phospholipids (FIG. 2, step d). The differences between the groups were made more apparent when the total content was used as an endogenous internal standard, which was due to decreased variability from factors such as sample quantity. 3) Peak ratios were obtained by comparing phospholipids, which were elevated with those that were diminished. (FIG. 2, step e). This novel quantitation approach amplified the subtle differences in phospholipid profiles to a level at which they could be used as diagnostic biomarkers in ovarian cancer.

Statistical Analysis.

Data were expressed as the mean±standard deviation (SD) for continuous variables. The ratios of phospholipids and lysophospholipids were compared using the Mann-Whitney U test for continuous variables, as appropriate. Receiver operating characteristic (ROC) analysis was performed and the area under the curve (AUC) was calculated for factors of the ratios of phospholipids and lysophospholipids in order to assess the accuracy of prediction of ovarian cancer for each factor. To test the stability of phospholipid and lysophospholipids species, the effects of storage time and incubation time on the phospholipid levels were examined using regression analysis with linear regression and Spearman's correlation coefficients. The p values of less than 0.05 were considered to be statistically significant. All analyses were performed using the SPSS software package (version 25.0 J SPSS).

Results

LC-MS Analysis of Phospholipids.

Representative total ion chromatogram and mass spectra of phospholipids and lysophospholipids in control samples is shown in FIG. 3. The peaks were identified by their retention time and MS and MS/MS data compared to standard phospholipids. The retention times of phospholipids and lysophospholipids are consistent with previous reports [Kim, 2013]. The total ion chromatogram shows major phospholipids present in human plasma, phosphatidylethanolamine (PE), phosphatidylinositol (PI), phosphatidylcholine (PC), and sphingomyelin (SM). Abundant lysophospholipids, LPC and LPE, are also visible in the total ion chromatogram. PE contains a significant amount of PEP, while PCP species account for only a minor portion of PC. A previous study showed PEP constituting up to half of the total PE in human plasma [Otoki, 2017], which is consistent with these observations. The MS spectra show that the PE, PC, and PI species contain common fatty acids, such as palmitic acid (16:0), stearic acid (18:0), oleic acid (18:1), linoleic acid (18:2), arachidonic acid (20:4), and docosahexaenoic acid (22:6). LPE and LPC also are constituted with these major fatty acids. SM contains myristic acid (14:0), arachidic acid (20:0), behenic acid (22:0), and nervonic acid (24:1). These are fatty acids commonly found in mammalian species, including humans. The present analysis is focused on major phospholipid species containing these common fatty acids. Less abundant phospholipids such as phosphatidylglycerol (PG) and phosphatidylserine (PS) were also found, but not included in this analysis due to their insufficient peak intensities, which may be inconsistently detected when interfered with by more abundant ions. LPA and LPI were also detected, but were found to be unstable, resulting in exclusion from this analysis.

Phospholipids Content.

Phosphatidylethanolamine (PE) and phosphatidylcholine (PC) are two major classes of phospholipids found in plasma. Each PE and PC is comprised of two types, diacyl and plasmenyl, denoted as diacyl PE and plasmenyl PE, and diacyl PC and plasmenyl PC. Using mass spectrometry, these phospholipids were measured in plasma from patients with benign cervical mass, patients with malignant ovarian cancer, and non-cancer controls. Compared to benign, diacyl PE content in cancer patients is higher whereas plasmenyl PE is lower without changing the total PE content. The ratio of diacyl PE/plasmenyl PE can distinguish between benign and malignant. Between control and malignant, a diacyl PC species in control is significantly higher without changing total PC. Therefore, diacyl PC/total PC can differentiate control from patients with cervical mass.

The contents of phospholipids were first compared by normalizing the intensities of individual peak areas to the areas of internal standards (Table 2). PME was used as an internal standard for phospholipid species. The ratio can be directly converted to concentration using a standard curve as previously shown [Kim, 2013]. LPE and LPC were normalized using LPE (17:1) and LPC (17:1), respectively. FIG. 3 shows the changes in the normalized total content of each class of phospholipids and lysophospholipids. The clean separation between different phospholipid species exemplifies the reliability of the method; low abundant molecules can be quantified due to the minimal to no interference of small peaks by other larger peaks giving a low probability of false positive results. Thus, the total PE content is ~40% higher in benign and cancer compared to control. SM was higher by ~20% in benign and cancer. LPE is 30% lower in benign and 15% lower in cancer compared to baseline. LPC is ~20% lower in benign and cancer than controls. Overall, phospholipids contents are generally higher in benign and cancer than control, whereas lysophospholipids contents are lower in benign and cancer. However, there is no significant difference in the content of phospholipids or lysophospholipids between benign and cancer.

Figure 4:
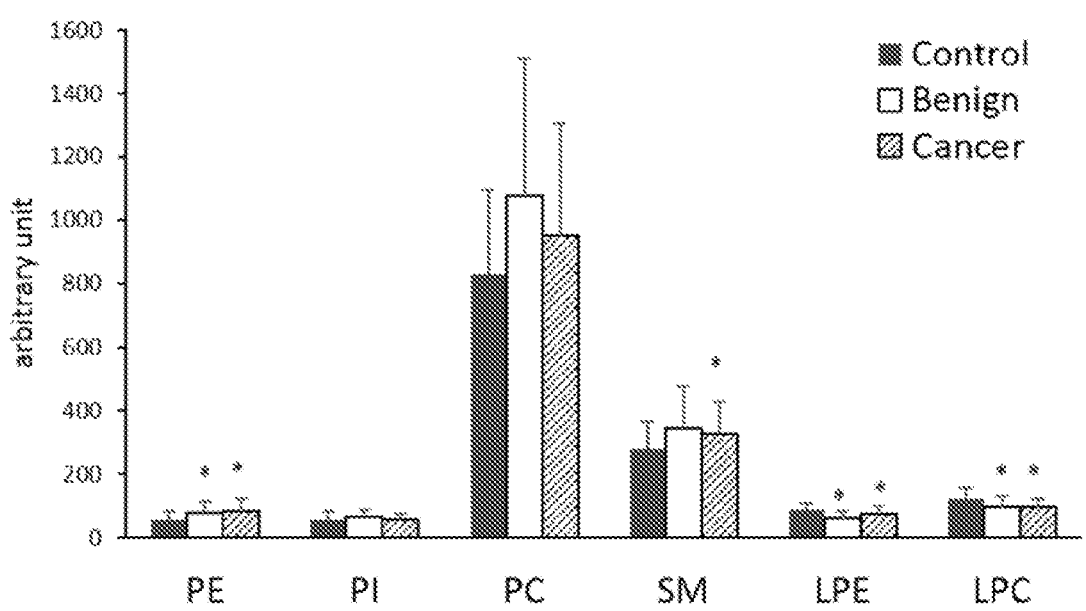
FIG. 4. Content of individual classes of phospholipids and lysophospholipids. PE, phosphatidylethanolamine; PI, phosphatidylinositol; PC, phosphatidylcholine; SM, sphingomyelin; LPE, lysophosphatidylethanolamine; LPC, lysophosphatidylcholine. *=$p<0.05$ when compared to control. Columns from left to right in each cluster of three columns represent Control, Benign and Cancer, respectively.

Changes in the content of individual phospholipids and lysophospholipids species were also analyzed. Firstly, the peak areas of individual phospholipids were normalized to corresponding internal standards (Table 2). There is a difference in the content of individual phospholipids between the three groups. PE species are generally higher in cancer plasma than control and benign, whereas PEP is higher in benign than control or cancer. This result indicates that the increased total PE shown in FIG. 4 may be due to increased diacyl PE in cancer, while it is mainly due to increased PEP in benign.

Table 2 also shows that multiple PC and PI species are higher in benign than the other two groups, whereas only PI18:1/20:4, PE16:0/18:1, PI18:0/20:4, and PI16:0/18:1 are found to be significantly different between benign and cancer (Table 2). However, these species lack the sensitivity and specificity to distinguish between cancer and benign.

As an alternative approach, the peak areas of individual phospholipids were normalized to the total content of phospholipids, where the total content of phospholipid serves as an endogenous internal standard. This approach is to identify individual species with the most significant change by reducing sample amount variations that exogenous internal standards cannot correct [Tokuyama, 1999]. As shown in Table 3, more metabolites were found with statistically significant difference. Various species in PC, PI, PE, plasmalogens are found to be different between control vs benign and control vs cancer, showing that ovarian cancer significantly alters phospholipid profiles in plasma. Differences were also found between benign vs cancer, particularly in SM and PE.

Between control and cancer, LPE and LPC, including LPEP and LPCP species, show the most significant differences. PC and SM were also found to be useful to differentiate cancer from control. In general, species containing long chain fatty acids (14 to 18 carbons) are lower in cancer unlike species containing very long chain fatty acids (>18 carbons). Between benign and cancer, PE and SM species show the most difference; PEP are lower in cancer, whereas PE are lower in benign. The results show significant differences in the content of metabolites, substantiating the notion that phospholipid species are interrelated and there is a degree of regulation that exists in the tissues, which gets dysregulated during tumorigenesis. Although variations were significantly reduced by normalization to the total content of each class of phospholipids and some species displayed excellent sensitivity and specificity to distinguish between control and ovarian cancer, none of the species were able to be used to distinctly distinguish between benign and control, and benign and cancer.

Normalization to Other Species within a Class.

The amount of one species was normalized to another species within the same class. In order to accomplish this, species were chosen whose content was either increased in one situation and decreased in another, and determined the ratio between these two species. Using this approach, multiple combinations were identified that showed excellent separation between the three groups. For example, the ratio of SM 18:1/24:1 was lower in cancer than in benign, but SM 18:1/14:0 was higher in cancer. Therefore, the ratio of SM 18:1/24:1/SM 18:1/22:0 was significantly high in cancer.

Figure 5A:
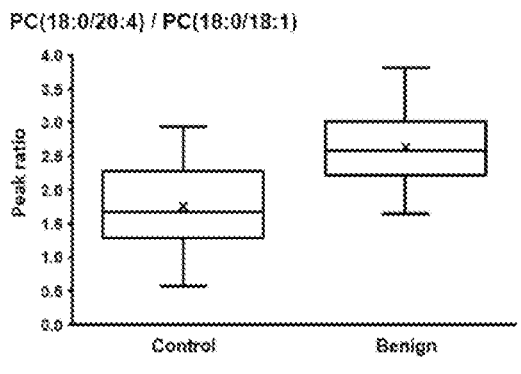
FIG. 5A-5F. A) Peak ratios of PC18:0/20:4/PC18:0/18:1 in Controls and Benign. B) The area under the curve (AUC) of the capacity of the ratios of PC18:0/20:4/PC18:0/18:1 to differentiate benign from control was 0.87. C) Peak ratios of LPC20:4/LPC18:0 in Controls and Cancer. D) The AUC of the capacity of the ratios of LPC20:4/LPC18:0 to differentiate cancer from control was 0.95. E) Peak ratios of SM18:1/24:1/SM18:1/22:0 in Benign and Cancer. F) The AUC of the capacity of the ratios of SM18:1/24:1/SM18:1/22:0 to differentiate benign from control was 0.84. Preferred AUC values are in the range of 0.8-1.0; more preferred AUC values are in the range of 0.9-1.0.
Figure 5B:
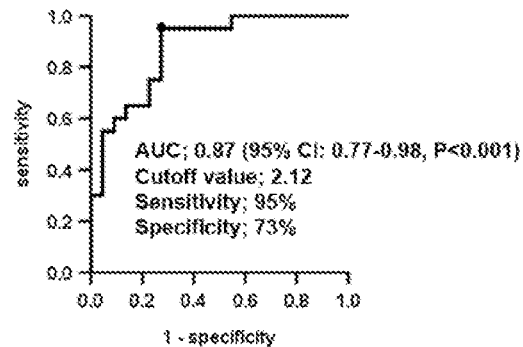
Figure 5C:
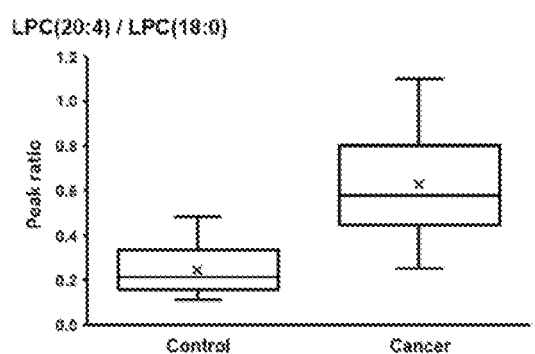
Figure 5D:
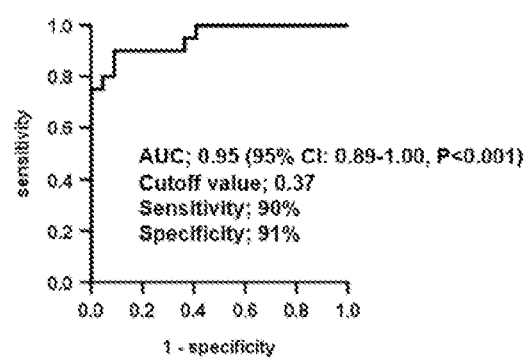
Figure 5E:
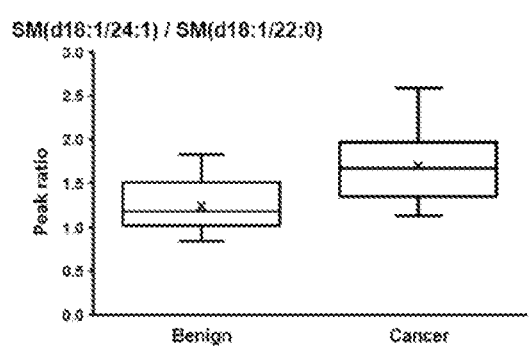
Figure 5F:
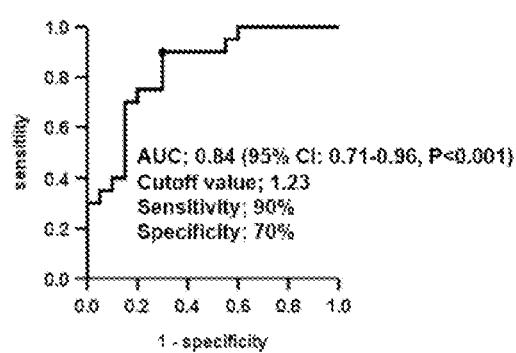

In this way, Table 4 was developed based on the above algorithm from Table 3. The AUCs, their 95% confidence intervals (CI), p values, sensitivities, specificities, and cutoff values for control vs benign, control vs cancer, and benign vs cancer are given in Table 4. FIG. 5A-5B showed that the best AUC of the ratios of PC18:0/20:4/PC18:0/18:1 that has the capacity to differentiate benign from control was 0.87 (95% CI: 0.77-0.98, P<0.001) with a cutoff value of 2.12, a sensitivity of 95%, and a specificity of 73%. FIG. 5C-5D showed that the best AUC of the ratios of LPC20:4/LPC18:0 that had the capacity to differentiate cancer from control was 0.95 (95% CI: 0.89-1.00, P<0.001) with a cutoff value of 0.37, a sensitivity of 90%, and a specificity of 91%. FIG. 5E-5F showed that the best AUC of the ratios of SM18:1/24:1/SM18:1/22:0 that had the capacity to differentiate benign from control was 0.84 (95% CI: 0.71-0.96, P<0.001) with a cutoff value of 1.23, a sensitivity of 90%, and a specificity of 70%.

No Changes in the Ratio Occur when the Sample Amount is Altered.

To demonstrate the applicability of the ratio, we examined the changes in the ratio by altering the sample amount. The species in each class of phospholipids and lysophospholipids have essentially the same response despite using various amounts of sample. This result exhibits that the ratios of the species are unaffected by the amount in the range of detection used in the method, which incorporates above physiological concentrations.

Detection of Additional Cancers.

The markers that were developed to detect ovarian cancer were also tested to determine if they could detect other cancers. In general, these markers could also recognize other cancers. However, some markers are more sensitive to specific cancers. FIG. 6 shows that the ratio of SM 18:1/18:0/SM 18:1/14:0 is elevated in all cancer type tested compared to the control. Readings were highest in pancreatic cancer, showing that the ratio of SM 18:1/18:0/SM 18:1/14:0 is particularly useful in detecting pancreatic cancer.

To further assess the diagnostic power of the ratio of SM 18:1/18:0/SM 18:1/14:0 in detecting pancreatic cancer, ROC analysis was performed. FIG. 7 shows that the ratio of SM 18:1/18:0/SM 18:1/14 can identify pancreatic cancer with a 100% sensitivity and a 96% specificity.

Therefore, the ratios using paired phospholipid markers may be used to screen for the presence of certain cancers as well as to diagnose a specific cancer.

Discussion

Multiple phospholipid markers were identified that can distinguish between control vs benign, control vs cancer, and benign vs cancer, with excellent sensitivity and/or specificity. The existence of multiple markers allows options to choose for the best marker based on the purpose of diagnosis, e.g. control vs cancer or benign vs cancer. Phospholipids and lysophospholipids studied in these experiments were stable under the conditions commonly used to process clinical samples. Overall, the results demonstrate that phospholipids have a great potential to serve as novel diagnostic markers for ovarian and pancreatic cancers.

Despite substantial advances in understanding cancer pathology, the survival of ovarian cancer patients has not been significantly improved in the last 20 years. One of the reasons is the lack of diagnostic biomarkers for detection of ovarian cancer at early stages. Since the survival rate of patients is over 90% when diagnosed at stages I and II, and only ~30% when diagnosed at advanced stage, early diagnosis is imperative. Additionally, benign ovarian tumors most commonly occur in women of childbearing age. It is important for patients with adnexal masses to protect their ovarian function for any future pregnancies by determining the status of their masses less invasively. Although immediate surgical treatment is required, such as torsion and rupture, benign ovarian tumors can often be managed, with serial imaging and, potentially, hormone suppression [Gonzalez, 2017]. The decision to receive surgical treatment can be made based on the patient's symptoms, physical examination, and imaging studies, including ultrasonography, computed tomography and magnetic resonance imaging. Additionally, biomarkers that can distinguish between a benign mass from cancer are needed to avoid unnecessary surgical removal of ovaries, which would impede in childbirth and adversely influence hormone levels.

Cytokines, proteases, and hormones have been tested for their use as non-invasive diagnostic indicators in ovarian cancer, but no single marker has shown sufficient sensitivity and specificity for clinical use. Therefore, effort has been shifted to the development of algorithms using combinations of multiple markers to improve the diagnostic power. This algorithm-based approach has proven to be more efficient; however, there still is a need for identification of better markers either used individually or as a component of a larger algorithm. The present invention addresses this need.

One advantage of phospholipids as a biomarker is the availability of total content or individual content of phospholipids for sample normalization. Normalization is an important step for quantitative analysis to find true concentration differences between groups of samples. Quantitation is a process of sequential normalization of measured peak intensities of metabolites of interest to the peak intensities of internal standards, or to a response curve generated using standard materials and internal standards. This is the commonly used method to calculate the concentrations of metabolites. The use of an internal standard significantly reduces variations generated during sample preparation and analysis. However, sample amount variations, which cannot be corrected by the use of an internal standard, have a more significant interference than simple analytical variations [Wu, 2016]. Therefore, the calculated concentrations often have to be normalized to the amounts of samples, or other indicators of the amount. Preferably, the use of endogenous internal standards will correct both the analytical variations and the amount variations.

The ratio of two related phospholipids species was used, where one species serves as an endogenous internal standard. The use of the ratio significantly reduces the individual variations when compared to the concentrations of individual species. The use of ratio also removes the use of internal standards for each target lipid species, significantly simplifying assay preparation and normalization. In fact, Table 4 shows that LPE22:6/LPEP 16:0 has the best sensitivity in distinguishing between control and benign, SM18:1/24:1/SM18:1/22:0 has the best sensitivity between control and ovarian cancer, and PE16:0/18:1/PEP18:0/18:2 has the best specificity in distinguishing between benign and ovarian cancer. The ratio of SM 18:1/18:0/SM 18:1/14 can identify pancreatic cancer with a 100% sensitivity and a 96% specificity (FIG. 7).

In conclusion, ion-trap mass spectrometry was used to survey with high sensitivity and specificity for all major phospholipids and lysophospholipids circulating in plasma. Multiple useful biomarkers were identified upon transforming concentration data into the ratios between two species within a class. Since peak area was used for quantifications, the phospholipid pairs were limited to the same classes of lipids, due to possible different responses of different classes that may alter the ratio when analyzed using different types of mass spectrometers or sample amounts. However, the ratio can be applied to species between different classes, further improving upon the power of this methodology. The use of ratios between two species does not require the maintenance of an internal standard and standard materials for rigorous quantitation. Combined with simple sample preparation steps, monitoring changes in the ratios may be highly practical and useful for screening women for the presence of ovarian cancer and treating those identified as having ovarian cancer in accordance with the current best medical practices, as well as for screening and treating people for pancreatic cancer. Likewise, monitoring changes in the ratios may be highly practical and useful for screening women for the presence of benign adnexal masses and treating those identified as having benign tumors in accordance with the current best medical practices.

TABLE 1

Characteristics in patients with ovarian cancer and benign ovarian tumor.

| | Control (n = 22) | Benign (n = 20) | Cancer (n = 20) | P value |
|---|---|---|---|---|
| Age median (IQR)* | 57 (52-59) | 56 (52-65) | 63 (55-69) | 0.052 |
| FIGO stage | | | | |
| I | — | — | 3 | |
| II | — | — | 1 | |
| III | — | — | 15 | |
| IV | — | — | 1 | |
| Histologic type | | | | |
| Serious | — | 8 | 9 | |
| Mucinous | — | 2 | 1 | |
| Endometrioid | — | 3 | 3 | |
| Unclassified | — | 6 | 7 | |

*IQR, interquartile range. The age was recorded from 17 controls.

TABLE 2

The content of phospholipids by normalizing the intensities of individual peak areas to the areas of internal standards.

| Control (Con) vs Benign (Ben) | | | Control (Con) vs Cancer (Can) | | | Benign (Ben) vs Cancer (Can) | | |
|---|---|---|---|---|---|---|---|---|
| Species | Ben/Con | P value | Species | Can/Con | P value | Species | Can/Ben | P value |
| LPEP16:0 | 0.368 | 0.000 | PE16:0/22:6 | 3.155 | 0.000 | PI18:1/20:4 | 0.718 | 0.014 |
| PE16:0/22:6 | 1.832 | 0.000 | PE18:0/22:6 | 2.606 | 0.000 | PE16:0/18:1 | 1.544 | 0.016 |
| PI18:0/22:6 | 1.889 | 0.001 | LPE22:6 | 1.822 | 0.000 | PI18:0/20:4 | 0.787 | 0.040 |
| PEP16:0/22:6 | 1.774 | 0.001 | LPC22:6 | 2.276 | 0.000 | PI16:0/18:1 | 0.693 | 0.042 |
| LPC18:0 | 0.661 | 0.001 | PC18:0/22:6 | 1.754 | 0.000 | LPC22:6 | 1.460 | 0.055 |
| PC16:0/22:6 | 1.779 | 0.001 | PC16:0/22:6 | 1.779 | 0.000 | SM18:1/14:0 | 0.724 | 0.055 |
| LPE18:1 | 0.621 | 0.001 | LPE18:2 | 0.648 | 0.001 | PI16:0/20:4 | 0.746 | 0.055 |
| PEP18:0/22:6 | 1.889 | 0.001 | LPE18:1 | 0.618 | 0.001 | SM18:1/23:0 | 0.835 | 0.066 |

TABLE 3

The content of phospholipids by normalizing the intensities of individual peak areas to the total content of phospholipids.

| Control (Con) vs Benign (Ben) | | | Control (Con) vs Cancer (Can) | | | Benign (Ben) vs Cancer (Can) | | |
|---|---|---|---|---|---|---|---|---|
| Species | Ben/Con | P value | Species | Can/Con | P value | Species | Can/Ben | P value |
| LPE20:4 | 1.551 | 0.000 | LPC20:4 | 2.086 | 0.000 | SM18:1/24:1 | 1.196 | 0.000 |
| LPE22:6 | 2.134 | 0.000 | PC18:0/18:1 | 0.771 | 0.000 | SM18:1/22:0 | 0.873 | 0.001 |
| LPE22:5 | 1.659 | 0.000 | LPE22:6 | 2.168 | 0.000 | PC18:0/18:1 | 0.888 | 0.002 |
| PC18:0/20:4 | 1.321 | 0.000 | LPC22:6 | 2.758 | 0.000 | SM18:1/14:0 | 0.790 | 0.002 |
| LPC22:6 | 1.907 | 0.000 | LPC18:0 | 0.811 | 0.000 | LPE18:2 | 0.718 | 0.002 |
| PEP18:0/22:6 | 1.327 | 0.000 | LPC22:5 | 2.330 | 0.000 | PE16:0/18:1 | 1.434 | 0.006 |
| LPC20:4 | 1.706 | 0.000 | SM18:1/24:1 | 1.261 | 0.000 | SM18:2/22:0 | 0.903 | 0.007 |
| PCP18:0/20:4 | 1.322 | 0.000 | SM18:1/20:0 | 0.819 | 0.000 | SM18:1/23:0 | 0.866 | 0.008 |
| PI18:0/22:6 | 1.566 | 0.001 | PC16:0/20:4 | 1.420 | 0.000 | PEP18:0/18:2 | 0.732 | 0.008 |
| PI18:0/22:5 | 1.382 | 0.001 | PE16:0/22:6 | 2.182 | 0.000 | SM18:1/16:0 | 1.050 | 0.010 |
| PEP16:0/22:6 | 1.302 | 0.001 | PCP18:0/20:4 | 1.353 | 0.000 | PEP16:0/18:1 | 0.780 | 0.013 |
| PC18:0/22:6 | 1.382 | 0.002 | SM18:1/22:0 | 0.840 | 0.000 | LPC22:6 | 1.446 | 0.014 |
| LPC18:0 | 0.884 | 0.002 | PE18:0/22:6 | 1.939 | 0.000 | SM18:1/20:0 | 0.880 | 0.016 |
| PE18:0/18:1 | 0.633 | 0.002 | PI18:0/22:6 | 1.684 | 0.000 | PEP16:0/18:2 | 0.725 | 0.020 |
| PC16:0/18:1 | 1.233 | 0.002 | LPE20:4 | 1.370 | 0.000 | PE16:0/22:6 | 1.467 | 0.023 |
| PC18:0/18:1 | 0.868 | 0.002 | LPE22:5 | 1.589 | 0.000 | PC16:0/16:0 | 1.150 | 0.030 |
| PE16:0/22:6 | 1.487 | 0.003 | SM18:1/23:0 | 0.853 | 0.000 | LPC18:0 | 0.917 | 0.033 |
| PI18:0/20:4 | 1.178 | 0.003 | PC16:0/22:6 | 1.602 | 0.000 | PC16:0/20:4 | 1.151 | 0.035 |
| LPC22:5 | 1.823 | 0.003 | SM18:1/14:0 | 0.764 | 0.000 | PEP16:0/22:6 | 0.933 | 0.035 |

TABLE 4

The AUCs, their 95% confidence intervals (CI), p values, sensitivities, specificities, and cutoff values for a) control vs benign, b) control vs cancer, and c) benign vs cancer.

| a) Control vs Benign | PC18:0/20:4/ PC18:0/18:1 | LPE22:6/ LPEP16:0 | LPC22:6/ LPC18:0 | LPC20:4/ LPC18:0 | PC18:0/22:6/ PC18:0/18:1 |
|---|---|---|---|---|---|
| AUC | 0.87 | 0.86 | 0.85 | 0.84 | 0.83 |
| P value | <0.001 | <0.001 | <0.001 | <0.001 | <0.001 |
| 95% CI | 0.77-0.98 | 0.74-0.97 | 0.72-0.97 | 0.72-0.96 | 0.71-0.96 |

TABLE 4-continued

The AUCs, their 95% confidence intervals (CI), p values, sensitivities, specificities, and cutoff values for a) control vs benign, b) control vs cancer, and c) benign vs cancer.

| Sensitivity (%) | 95 | 100 | 80 | 65 | 90 |
|---|---|---|---|---|---|
| Specificity (%) | 73 | 64 | 86 | 91 | 68 |
| Cutoff value | 2.12 | 3.9 | 0.07 | 0.37 | 0.35 |

| b) Control vs Cancer | LPC20:4/ LPC18:0 | LPC22:6/ LPC18:0 | LPC20:4/ LPC16:0 | LPC22:6/ LPCP16:0 | SM18:1/24:1/ SM18:1/22:0 |
|---|---|---|---|---|---|
| AUC | 0.95 | 0.94 | 0.94 | 0.92 | 0.92 |
| P value | <0.001 | <0.001 | <0.001 | <0.001 | <0.001 |
| 95% CI | 0.89-1.00 | 0.88-1.00 | 0.87-1.00 | 0.84-1.00 | 0.83-1.00 |
| Sensitivity (%) | 90 | 95 | 80 | 95 | 100 |
| Specificity (%) | 91 | 82 | 96 | 82 | 73 |
| Cutoff value | 0.37 | 0.07 | 0.14 | 4 | 1.13 |

| c) Benign vs Cancer | SM18:1/24:1/ SM18:1/22:0 | SM18:1/16:0/ SM18:1/22:0 | SM18:1/16:0/ SM18:1/14:0 | SM18:1/24:1/ SM18:1/14:0 | PE16:0/18:1/ PEP18:0/18:2 |
|---|---|---|---|---|---|
| AUC | 0.84 | 0.82 | 0.82 | 0.81 | 0.77 |
| P value | <0.001 | <0.001 | 0.001 | 0.001 | 0.003 |
| 95% CI | 0.71-0.96 | 0.70-0.95 | 0.68-0.96 | 0.66-0.95 | 0.62-0.92 |
| Sensitivity (%) | 90 | 90 | 80 | 80 | 55 |
| Specificity (%) | 70 | 65 | 80 | 85 | 100 |
| Cutoff value | 1.23 | 2.41 | 11.3 | 6.24 | 0.47 |

REFERENCES

Biggs W S, Marks S T. Diagnosis and Management of Adnexal Masses. American family physician. 2016; 93:676-81.
Choi J, Yin T, Shinozaki K, Lampe J W, Stevens J F, Becker L B, et al. Comprehensive analysis of phospholipids in the brain, heart, kidney, and liver: brain phospholipids are least enriched with polyunsaturated fatty acids. Mol Cell Biochem. 2018; 442:187-201.
De Angelis R, Sant M, Coleman M P, Francisci S, Baili P, Pierannunzio D, et al. Cancer survival in Europe 1999-2007 by country and age: results of EUROCARE—5-a population-based study. The Lancet Oncology. 2014; 15:23-34.
Gonzalez D O, Minneci P C, Deans K J. Management of benign ovarian lesions in girls: a trend toward fewer oophorectomies. Curr Opin Obstet Gynecol. 2017; 29:289-94.
Jackson D, Craven R A, Hutson R C, Graze I, Lueth P, Tonge R P, et al. Proteomic profiling identifies afamin as a potential biomarker for ovarian cancer. Clin Cancer Res. 2007; 13:7370-9.
Kim J, Hoppel C L. Comprehensive approach to the quantitative analysis of mitochondrial phospholipids by HPLC-MS. J Chromatogr B Analyt Technol Biomed Life Sci. 2013; 912:105-14.
Kim J, Lampe J W, Yin T, Shinozaki K, Becker L B. Phospholipid alterations in the brain and heart in a rat model of asphyxia-induced cardiac arrest and cardiopulmonary bypass resuscitation. Mol Cell Biochem. 2015; 408:273-81.
Montagnana M, Benati M, Danese E. Circulating biomarkers in epithelial ovarian cancer diagnosis: from present to future perspective. Ann Transl Med. 2017; 5:276.
Otoki Y, Kato S, Kimura F, Furukawa K, Yamashita S, Arai H, et al. Accurate quantitation of choline and ethanolamine plasmalogen molecular species in human plasma by liquid chromatography-tandem mass spectrometry. J Pharm Biomed Anal. 2017; 134:77-8
Petricoin E F, Ardekani A M, Hitt B A, Levine P J, Fusaro V A, Steinberg S M, et al. Use of proteomic patterns in serum to identify ovarian cancer. Lancet. 2002; 359:572-7.
Santaballa A, Barretina P, Casado A, Garcia Y, Gonzalez-Martin A, Guerra E, et al. SEOM Clinical Guideline in ovarian cancer (2016). Clin Transl Oncol. 2016; 18:1206-12.
Schwartz P E, Taylor K J. Is early detection of ovarian cancer possible? Annals of medicine. 1995; 27:519-28.
Tokuyama W, Hashimoto T, Li Y X, Okuno H, Miyashita Y. Quantification of neurotrophin-3 mRNA in the rat hippocampal subregions using the RT-PCR-based coamplification method. Brain Res Brain Res Protoc. 1999; 4:407-14.
Wu Y, Li L. Sample normalization methods in quantitative metabolomics. J Chromatogr A. 2016; 1430:80-95.
Ye B, Cramer D W, Skates S J, Gygi S P, Pratomo V, Fu L, et al. Haptoglobin-alpha subunit as potential serum biomarker in ovarian cancer: identification and characterization using proteomic profiling and mass spectrometry. Clin Cancer Res. 2003; 9:2904-11.
Ye B, Skates S, Mok S C, Horick N K, Rosenberg H F, Vitonis A, et al. Proteomic-based discovery and characterization of glycosylated eosinophil-derived neurotoxin and COOH-terminal osteopontin fragments for ovarian cancer in urine. Clin Cancer Res. 2006; 12:432-41.
Zhang Y, Liu Y, Li L, Wei J, Xiong S, Zhao Z. High resolution mass spectrometry coupled with multivariate data analysis revealing plasma lipidomic alteration in ovarian cancer in Asian women. Talanta. 2016; 150:88-96.
Zhao Z, Xu Y. An extremely simple method for extraction of lysophospholipids and phospholipids from blood samples. J Lipid Res. 2010; 51:652-9.

What is claimed is:
1. A method for screening for an ovarian cancer or a benign ovarian tumor in a patient comprising
obtaining or having obtained a plasma sample from the patient, and
performing or having performed an assay on the plasma sample to identify whether the patient has ovarian cancer or a benign ovarian tumor, wherein the patient is identified as having ovarian cancer if an assay of phospholipids having been obtained from the plasma sample from the patient determined one or both of i) or ii):
i) one or more of the ratio of lysophosphatidylcholine (LPC), LPC20:4/LPC18:0, LPC22:6/LPC18:0, LPC20:4/LPC16:0, LPC22:6/lysophosphatidylcholine plasmalogen(LPCP)16:0, and/or sphingomyelin(SM), SM18:1/24:1/SM18:1/22:0, obtained from the plasma of the patient is elevated compared to the level from a control group of women without an ovarian tumor or ovarian cancer; or
ii) one or more of the ratio of sphingomyelin(SM), SM18:1/24:1/SM18:1/22:0, SM18:1/16:0/SM18:1/22:0, SM18:1/16:0/SM 18:1/14:0, SM18:1/24:1/SM18:1/14:0, and/or phosphatidylethanolamine (PE), PE16:0/18:1/PEP18:0/18:2 obtained from the plasma of the patient is elevated compared to the level from a group of women with a benign ovarian tumor; and
wherein the patient is identified as having a benign ovarian tumor if an assay of phospholipids having been obtained from the plasma sample from the patient determined one or more of the ratio of phosphatidylcholine (PC), PC18:0/20:4/PC18:0/18:1, lysophosphatidylethanolamine(LPE), LPE22:6/LPEP16:0, lysophosphatidylcholine(LPC), LPC22:6/LPC18:0, LPC20:4/LPC18:0 and/or PC18:0/22:6/PC18:0/18:1 obtained from the plasma of the patient is elevated compared to the level from a control group of women without an ovarian tumor or ovarian cancer;
wherein the phospholipids extracted from the plasma sample of the patient were analyzed using HPLC-mass spectrometry; and
wherein the phospholipids were normalized by a process comprising one or more of
normalizing peak areas to internal standards, where phospholipid species were normalized to 1,2-dipalmitoyl-sn-glycero-3-phospho-N-methylethanolamine (PME), and lysophosphatidylethanolamine (LPE) and lysophosphatidylcholine (LPC) species were normalized to LPE (17:1) and LPC (17:1), respectively;
individual phospholipid species were normalized to the total content of the class of phospholipids; and
peak ratios were obtained by comparing phospholipids.

2. The method of claim 1, wherein the patient is identified as having ovarian cancer if an assay of phospholipids having been obtained from the plasma sample from the patient determined that one or more of the ratio of lysophosphatidylcholine(LPC), LPC20:4/LPC18:0, LPC22:6/LPC18:0, LPC20:4/LPC16:0, LPC22:6/lysophosphatidylcholine plasmalogen(LPCP)16:0, and/or sphingomyelin(SM), SM18:1/24:1/SM18:1/22:0, obtained from the plasma of the patient is elevated compared to the level from a control group of women without an ovarian tumor or ovarian cancer.

3. The method of claim 1, wherein the patient is identified as having ovarian cancer if an assay of phospholipids having been obtained from the plasma sample from the patient determined that one or more of the ratio of sphingomyelin (SM), SM18:1/24:1/SM18:1/22:0, SM18:1/16:0/SM18:1/22:0, SM18:1/16:0/SM 18:1/14:0, SM18:1/24:1/SM18:1/14:0, and/or phosphatidylethanolamine (PE), PE16:0/18:1/PEP18:0/18:2 obtained from the plasma of the patient is elevated compared to the level from a group of women with a benign ovarian tumor.

4. The method of claim 1, wherein the patient is identified as having ovarian cancer if an assay of phospholipids having been obtained from the plasma sample from the patient determined that:
i) one or more of the ratio of lysophosphatidylcholine (LPC), LPC20:4/LPC18:0, LPC22:6/LPC18:0, LPC20:4/LPC16:0, LPC22:6/lysophosphatidylcholine plasmalogen(LPCP)16:0, and/or sphingomyelin(SM), SM18:1/24:1/SM18:1/22:0, obtained from the plasma of the patient is elevated compared to the level from a control group of women without an ovarian tumor or ovarian cancer; and
ii) one or more of the ratio of sphingomyelin(SM), SM18:1/24:1/SM18:1/22:0, SM18:1/16:0/SM18:1/22:0, SM18:1/16:0/SM 18:1/14:0, SM18:1/24:1/SM18:1/14:0, and/or phosphatidylethanolamine (PE), PE16:0/18:1/PEP18:0/18:2 obtained from the plasma of the patient is elevated compared to the level from a group of women with a benign ovarian tumor.

5. The method of claim 1, wherein the patient is identified as having a benign ovarian tumor if an assay of phospholipids having been obtained from the plasma sample from the patient determined that one or more of the ratio of phosphatidylcholine (PC), PC18:0/20:4/PC18:0/18:1, lysophosphatidylethanolamine(LPE), LPE22:6/LPEP16:0, lysophosphatidylcholine(LPC), LPC22:6/LPC 18:0, LPC20:4/LPC 18:0 and/or PC18:0/22:6/PC18:0/18:1 obtained from the plasma of the patient is elevated compared to the level from a control group of women without an ovarian tumor or ovarian cancer.

\* \* \* \* \*